(12) United States Patent
Schudlo

(10) Patent No.: US 11,741,694 B2
(45) Date of Patent: Aug. 29, 2023

(54) SPINAL FRACTURE DETECTION IN X-RAY IMAGES

(71) Applicant: MERATIVE US L.P., Ann Arbor, MI (US)

(72) Inventor: Larissa Christina Schudlo, Boston, MA (US)

(73) Assignee: MERATIVE US L.P., Ann Arbor, MI (US)

( * ) Notice: Subject to any disclaimer, the term of this patent is extended or adjusted under 35 U.S.C. 154(b) by 502 days.

(21) Appl. No.: 16/897,225

(22) Filed: Jun. 9, 2020

(65) Prior Publication Data

US 2021/0383536 A1 Dec. 9, 2021

(51) Int. Cl.
*G06V 10/82* (2022.01)
*G06T 7/00* (2017.01)
(Continued)

(52) U.S. Cl.
CPC .............. *G06V 10/82* (2022.01); *G06F 18/22* (2023.01); *G06F 18/243* (2023.01); *G06N 3/02* (2013.01);
(Continued)

(58) Field of Classification Search
CPC ..................... G06T 7/0012; G06T 7/70; G06T 2207/10116; G06T 2207/20021;
(Continued)

(56) References Cited

U.S. PATENT DOCUMENTS

| 6,608,916 B1 | 8/2003 | Wei et al. |
| 7,046,830 B2 | 5/2006 | Gerard et al. |

(Continued)

FOREIGN PATENT DOCUMENTS

| WO | 2008/116918 A1 | 10/2008 |
| WO | 2009/124995 A1 | 10/2009 |

(Continued)

OTHER PUBLICATIONS

Chettrit et al., "3D Convolutional Sequence to Sequence Model for Vertebral Compression Fractures Identification in CT", arXiv: 2010.03739v1, Oct. 8, 2020, pp. 1-11 (Year: 2020).*

(Continued)

*Primary Examiner* — Nay A Maung
*Assistant Examiner* — Jose M Torres
(74) *Attorney, Agent, or Firm* — Michael Best & Friedrich LLP

(57) ABSTRACT

Methods and systems for detecting a vertebral fracture within an x-ray. One method includes receiving a chest x-ray image and identifying a plurality of vertebrae represented in the chest x-ray image. The method further includes extracting a plurality of image patches from the chest x-ray image, each image patch of the plurality of image patches including a portion of the chest x-ray image representing one of the plurality of vertebrae identified in the chest x-ray image. The method further includes sequencing the plurality of image patches into an ordered sequence of image patches, and assigning, with a deep learning model applied to the ordered sequence of image patches, a classification to each of the plurality of image patches indicating whether the image patch represents a fractured vertebra or an unfractured vertebra.

20 Claims, 6 Drawing Sheets

(51) Int. Cl.
| | |
|---|---|
| *G16H 30/40* | (2018.01) |
| *G06N 3/02* | (2006.01) |
| *G06F 18/22* | (2023.01) |
| *G06F 18/243* | (2023.01) |
| *G06V 20/50* | (2022.01) |
| *G06T 7/70* | (2017.01) |

(52) U.S. Cl.
CPC .............. *G06T 7/0012* (2013.01); *G06T 7/70* (2017.01); *G06V 20/50* (2022.01); *G16H 30/40* (2018.01); *G06T 2207/10116* (2013.01); *G06T 2207/20084* (2013.01); *G06T 2207/30012* (2013.01)

(58) Field of Classification Search
CPC . G06T 2207/20081; G06T 2207/20084; G06T 2207/30012; G06T 2207/30168; G06K 9/6201; G06K 9/6279; G06N 3/02; G06N 3/0445; G06N 3/0454; G06N 3/08; G06N 7/005; G16H 30/40; G16H 50/20; G06V 10/82; G06V 20/50
See application file for complete search history.

(56) References Cited

U.S. PATENT DOCUMENTS

| | | | |
|---|---|---|---|
| 8,891,848 | B2 | 11/2014 | Blumfield et al. |
| 11,145,060 | B1* | 10/2021 | Schudlo ................. G16H 50/20 |
| 2003/0112921 | A1 | 6/2003 | Lang et al. |
| 2006/0110017 | A1 | 5/2006 | Tsai et al. |
| 2008/0216845 | A1 | 9/2008 | De Bruijne et al. |
| 2009/0169087 | A1 | 7/2009 | Doi et al. |
| 2010/0135549 | A1 | 6/2010 | Pettersen et al. |
| 2011/0142307 | A1 | 6/2011 | Ghosh et al. |
| 2016/0113612 | A1 | 4/2016 | Sedlmair et al. |
| 2019/0239843 | A1 | 8/2019 | Bregman-Amitai et al. |
| 2019/0370957 | A1* | 12/2019 | Manickam ............. G06V 10/82 |
| 2020/0160515 | A1* | 5/2020 | Chabin ................. G06V 10/82 |
| 2021/0097678 | A1* | 4/2021 | Dutta ................... G06N 3/0454 |
| 2022/0051398 | A1* | 2/2022 | Watanabe ................ G06T 7/11 |

FOREIGN PATENT DOCUMENTS

| | | |
|---|---|---|
| WO | 2019/106061 A1 | 6/2019 |
| WO | 2019/200349 A1 | 10/2019 |

OTHER PUBLICATIONS

Burns et al., "Automated detection, localization and classification of traumatic vertebral body fractures in the thoracic and lumbar spine at CT," Radiology, Jan. 2016, vol. 278, No. 1, 64-73.

Gale et al., "Detecting hip fractures with radiologist-level performance using deep neural networks," (Submitted on Nov. 17, 2017), https://arxiv.org/abs/1711.06504.

Huang et al., "An improved level set method for vertebra CT image segmentation," BioMedical Engineering OnLine, May 2013, 12:48.

Lessmann et al., "Iterative fully convolutional neural networks for automatic vertebra segmentation and identification," (Submitted on Apr. 12, 2018), https://arxiv.org/abs/1804.04383.

Nicolaes et al., "Detection of vertebral fractures in CT using 3D Convolutional Neural Networks," (Submitted on Nov. 5, 2019), https://arxiv.org/abs/1911.01816.

Raghavendra et al., "Automated system for the detection of thoracolumbar fractures using a CNN architecture," Future Generation Computer Systems, Aug. 2018, vol. 85, 184-189.

Ribeiro et al., "Detection of vertebral compression fractures in lateral lumbar X-ray images," In: XXIII Congresso Brasileiro em Engenharia Biomedica-XXIII CBEB, Oct. 2012, pp. 1136-1139.

Roth et al., "Deep convolutional networks for automated detection of posterior-element fractures on spine CT," (Submitted on Jan. 29, 2016), https://arxiv.org/abs/1602.00020v1.

Zareie et al., "Automatic segmentation of vertebrae in 3D CT images using adaptive fast 3D pulse coupled neural networks," Australasian physical & engineering sciences in medicine / supported by the Australasian College of Physical Scientists in Medicine and the Australasian Association of Physical Sciences in Medicine 41(4):1009-1020.

* cited by examiner

SPINAL FRACTURE DETECTION IN X-RAY IMAGES

FIELD

Embodiments described herein relate to systems and methods for detecting vertebral fractures in x-ray images, such as frontal and lateral x-ray images. For example, some embodiments use a combination of image processing and artificial intelligence techniques to identify individual vertebra and the visibility of each vertebra within an x-ray image. The vertebrae are then considered as an ordered sequence to identify fractures by analyzing relative morphologies, such as through the use of a time-distributed convolutional neural network.

SUMMARY

In clinical practice, frontal and lateral chest x-rays may be ordered for a variety of reasons. On these routinely performed chest x-rays, spine fractures are frequently missed by clinicians. Vertebral spine fractures are particularly challenging to detect on frontal (anterior-posterior/posterior-anterior (AP/PA)) x-rays views. In particular, spinal fractures are different from fractures in other types of bones. Rather than presenting as a break or discontinuity, many spine fractures present as a vertebral body shape deformity or reduction in height beyond a predetermined threshold value, which makes the detection of vertebral fractures more challenging than other types of bone fractures. For example, a vertebral fracture must be distinguished from natural age-related degeneration, which varies considerably across individuals. Detection of vertebral spine fractures in standard chest x-rays is also challenged by a variety of factors, including the reading clinician's experience level, image quality, vertebrae visibility (vertebrae can be obstructed by foreign objects or the patient's own anatomy), and variability in what is visible in a given image (number of vertebra or region of the spine imaged).

Accordingly, there is a need for systems and methods configured to automatically detect the presences of one or more vertebral fracture in an x-ray image, while being robust to patient- or age-related variability as well as variations on vertebral visibility, the number of vertebra present in the image, and the portion of the spine imaged.

Embodiments described herein provide an automated solution for detecting vertebral body fractures in standard frontal and lateral x-rays using a combination of image processing and artificial intelligence techniques, which eliminates the need for specific types of images, such as computed tomography (CT) images or other higher-quality images that may not be available in some situations.

For example, embodiments described herein may provide a pipeline (e.g., an inference pipeline) that includes one or more models, such as neural networks, configured to identify vertebral fractures by isolating individual vertebra, evaluating the visibility of each vertebra, and considering vertebra with sufficient visibility as an ordered sequence in a time-distributed inference model to identify fractures by analyzing relative morphologies. In some embodiments, the proposed pipeline does not rely on complete visibility of all vertebrae or depend on a specific number of visible vertebra but instead accommodates variability in both of these factors. Such a pipeline offers a robust solution for detecting spinal fractures despite variations in visible anatomy, a patient's unique anatomy, and variations in imaging.

In particular, embodiments described herein provide systems and methods for detecting spinal fractures within x-ray images. For example, one embodiment provides a computer-implemented method of detecting fracture. The method includes receiving a chest x-ray image and identifying a plurality of vertebrae represented in the chest x-ray image. The method also includes extracting a plurality of image patches from the chest x-ray image. Each image patch of the plurality of image patches includes a portion of the chest x-ray image representing one of the plurality of vertebrae identified in the chest x-ray image. The method also includes sequencing the plurality of image patches into an ordered sequence of image patches, and assigning, with a deep learning model applied to the ordered sequence of image patches, a classification to each of the plurality of image patches indicating whether the image patch represents a fractured vertebra or an unfractured vertebra.

Another embodiment provides a system for detecting a fracture. The system comprises an electronic processor configured to receive a chest x-ray image and identify a plurality of vertebrae represented in the chest x-ray image. The electronic processor is further configured to extract a plurality of image patches from the chest x-ray image. Each image patch of the plurality of image patches includes a portion of the chest x-ray image representing one of the plurality of vertebrae identified in the chest image. The electronic processor is further configured to sequence the plurality of image patches into an ordered sequence of image patches, and assign, with a deep learning model applied to the ordered sequence of image patches, a classification to each of the plurality of image patches indicating whether the image patch represents a fractured vertebra or an unfractured vertebra.

A further embodiment provides a non-transitory computer-readable medium storing instructions that, when executed by an electronic processor, perform a set of functions. The set of functions includes receiving a chest x-ray image and identifying a plurality of vertebrae represented in the chest x-ray image. The set of functions further includes extracting a plurality of image patches from the chest x-ray image. Each image patch of the plurality of image patches includes a portion of the chest x-ray image representing one of the plurality of vertebrae identified in the chest x-ray image. The set of functions further includes sequencing the plurality of image patches into an ordered sequence of image patches, and assigning, with a deep learning model applied to the ordered sequence of image patches, a classification to each of the plurality of image patches indicating whether the image patch represents a fractured vertebra or an unfractured vertebra.

Other aspects will become apparent by consideration of the detailed description and accompanying drawings.

DETAILED DESCRIPTION

Before any embodiments are explained in detail, it is to be understood that the embodiments are not limited in their application to the details of construction and the arrangement of components set forth in the following description or illustrated in the following drawings. Other embodiments are capable of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or coupling, whether direct or indirect. Also, electronic communications and notifications may be performed using any known means including direct connections, wireless connections, etc.

A plurality of hardware and software based devices, as well as a plurality of different structural components may be utilized to implement the embodiments. In addition, embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the embodiments may be implemented in software (e.g., stored on non-transitory computer-readable medium) executable by one or more processors. As such, it should be noted that a plurality of hardware and software based devices, as well as a plurality of different structural components, may be utilized to implement the embodiments. For example, "mobile device," "computing device," and "server" as described in the specification may include one or more electronic processors, one or more memory modules including non-transitory computer-readable medium, one or more input/output interfaces, and various connections (e.g., a system bus) connecting the components.

Figure 1:
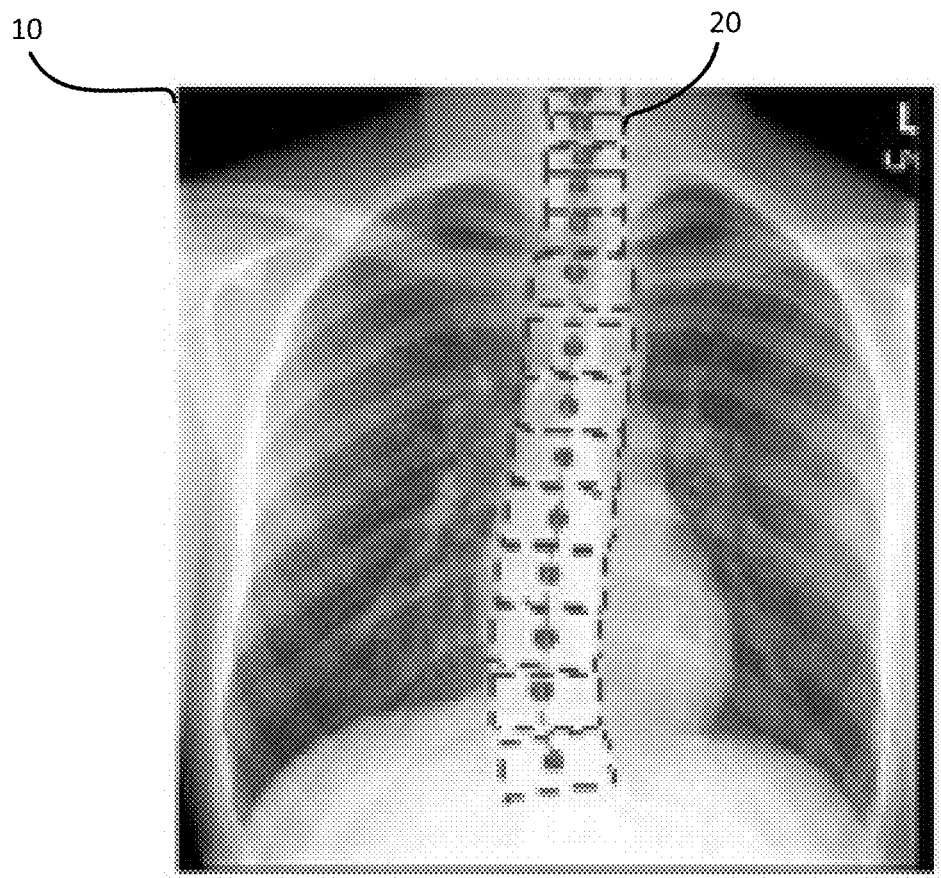
FIG. 1 illustrates a frontal chest x-ray image.

As described above in the Summary section, embodiments described herein provide an automated solution for detecting vertebral body fractures in x-ray images using a combination of image processing and artificial intelligence techniques. FIG. 1 illustrates an example frontal chest x-ray image 10. The image 10 includes a plurality of vertebrae 20, wherein each vertebra is represented by an image patch (a portion of the image 10). The plurality of vertebrae 20 and the image patches are annotated or marked in FIG. 1 for illustration purposes only (e.g., via a dot representing each vertebra and a dashed rectangle representing each image patch). However, it should be understood that, in practice, the x-ray image 10, as presented for processing, does not include such annotations. Each vertebra of the plurality of vertebrae 20 may or may not be fractured, and FIG. 2 described herein provides a method 100 for classifying each vertebra as being fractured or unfractured. The method 100 is described herein as being performed using the system 500 as described below (see FIG. 6) and, in particular, via one or more electronic processors 550 that implement one or more models, such as one or more neural networks.

Figure 2:
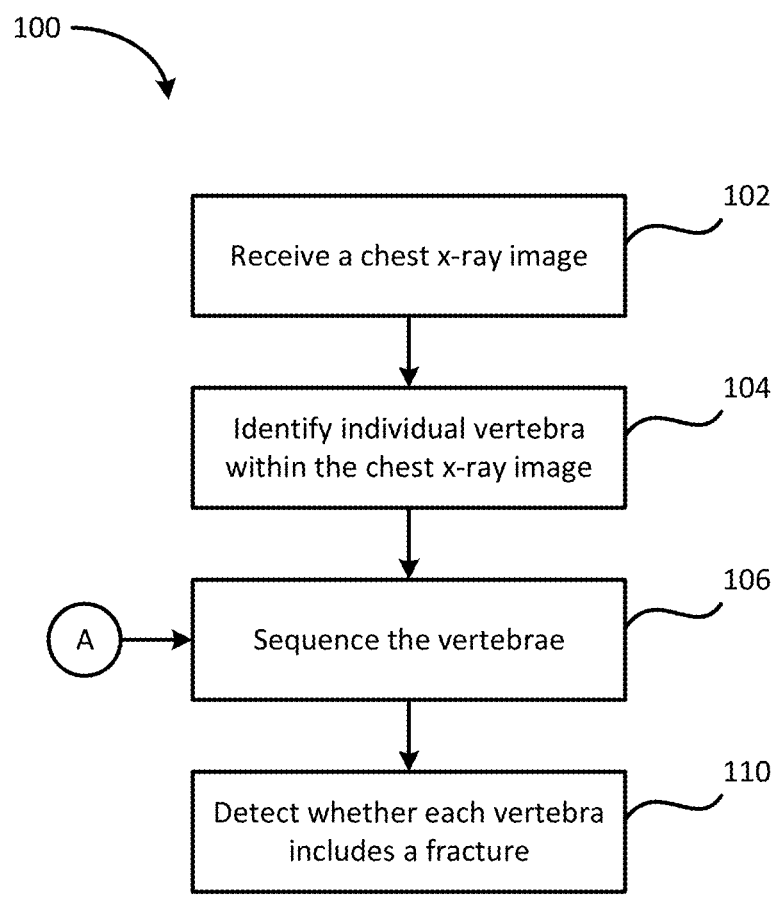
FIG. 2 illustrates a flowchart of a method of detecting vertebral fractures according to some embodiments.
Figure 4:
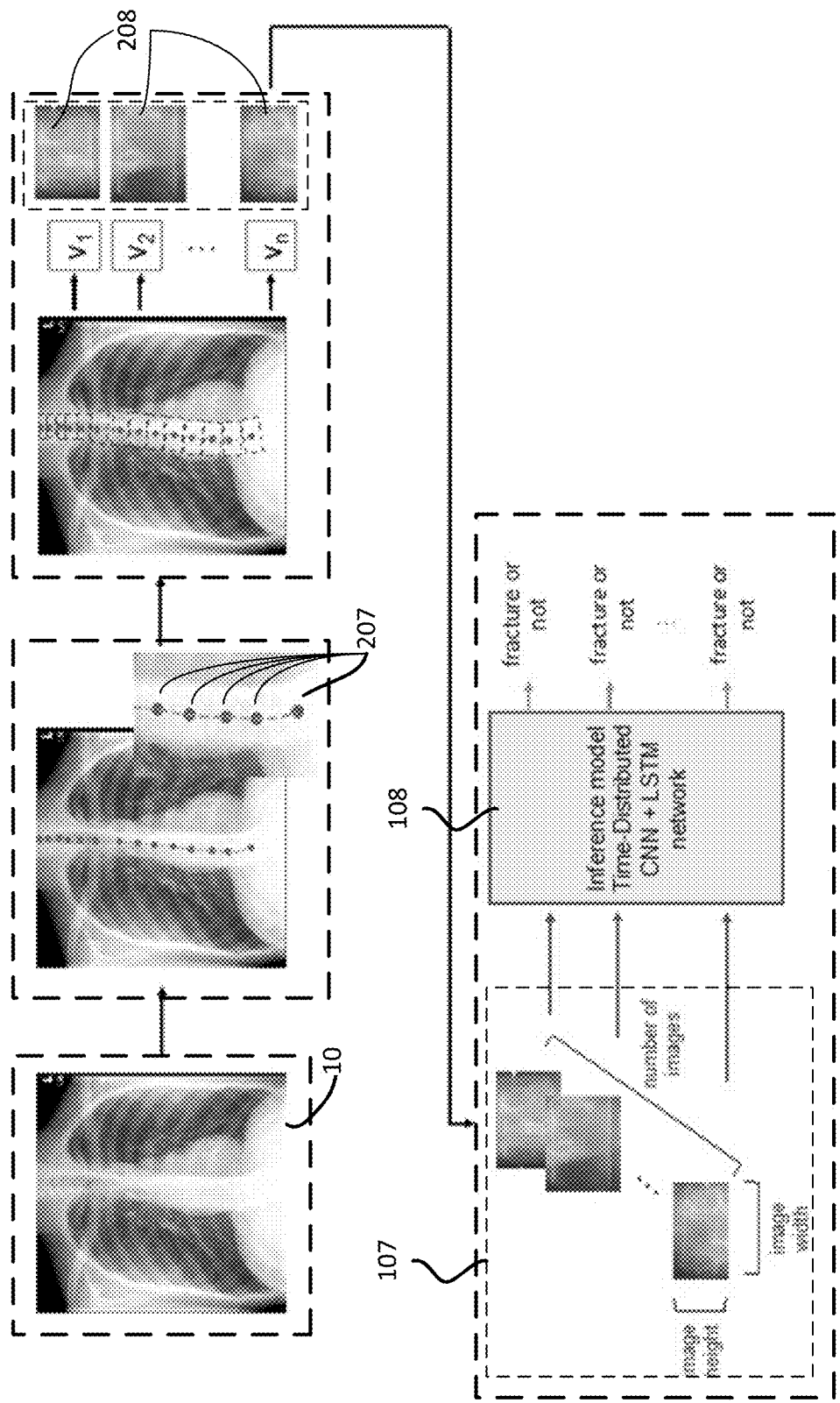
FIG. 4 illustrates an example frontal chest x-ray image being processed via the method of FIG. 2 according to some embodiments.

As illustrated in FIG. 2, the system 500 receives an x-ray, such as the example x-ray image 10 described above (at block 102). The chest x-ray image 10 may be received in a DICOM format. FIG. 4 illustrates the example x-ray image 10 and how the image 10 is processed as part of the method 100. Returning to FIG. 2, the system 500 identifies a plurality of vertebrae 20 included in the image 10 (at block 104). It should be understood that, in some embodiments, one or more pre-processes are performed on the chest x-ray image 10 before or as part of identifying the plurality of vertebrae 20. For example, various techniques may be used to prepare and enhance the chest x-ray image 10 for analysis, including performing image quality assessment, view detection, image normalization, or image down sampling (such as to a 1024×1024 pixel image) for a consistent image size.

Figure 3:
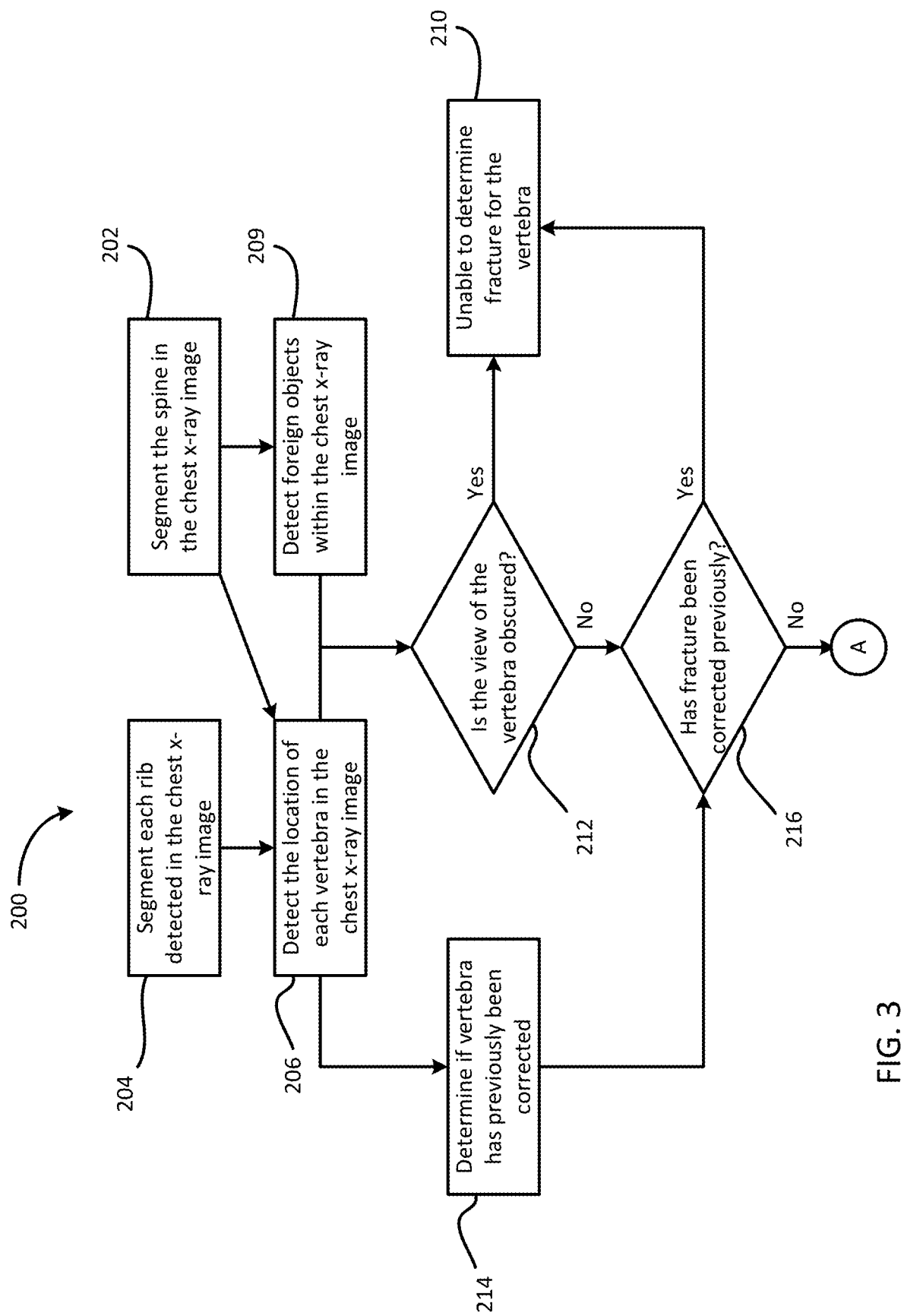
FIG. 3 illustrates a flowchart of a method of identifying individual vertebra within an x-ray image as part of the method of FIG. 2 according to some embodiments.

After any optional pre-processing techniques are performed, the system 500 identifies the plurality of vertebrae 20. It should be understood that different techniques can be used to identify the plurality of vertebrae 20. FIG. 3, however, illustrates one method 200 of identifying the plurality of vertebrae 20 within an image 10 according to some embodiments (as part of block 104). Again, the method 200 is described as being performed using the system 500 as described below. As illustrated in FIG. 3, at block 202, the system 500 segments the spine in the chest x-ray image 10. For example, a UNet model may be trained to detect and segment the spine in the chest x-ray image 10. In some embodiments, at block 204, the system 500 also segments and detects each rib in the x-ray image 10. The system 500 may also identify regions in which each detected rib connects to the detected spine. As described below, the detected spine and ribs may be used to detect the location of each vertebra, to assess whether a detected vertebra is adequate for fracture processing, to perform fracture detection, or a combination thereof.

At block 206, the system 500 detects the location of each vertebra in the chest x-ray image 10. For example, as illustrated in FIG. 4, the system 500 may identify a location (e.g., a central location) of each of a plurality of vertebrae 20 within the x-ray image 10. Each identified vertebra location is illustrated as a dot 207 in FIG. 4. Based on the determined location of each vertebra, an image patch 208 (see FIG. 4) may be identified within the image 10 (representing a portion or subset of the image 10). Accordingly, when n vertebrae ("v" as annotated in FIG. 4) are identified within the image 10, n associated image patches 208 are also identified. In some embodiments, each image patch 208 includes a portion of the chest x-ray image 10 representing a single vertebra. For example, each image patch 208 may fully include a detected vertebra and an associated intervertebral disc space above and below the identified vertebra, or the image patch may include a predetermined distance above and below the identified vertebra. However, in other embodiments, this distance may vary and may be dynamically set by the system 500, such as based on the detected anatomy, characteristics of the patient, or the like. Similarly, each image patch 208 may have a defined width that may be static or may be dynamically determined. In some embodiments, each image patch 208 is the same size. However, in other embodiments, the size of one or more of the patches 208 may vary.

In some embodiments, the system 500 uses an object detection model to detect the location of each vertebra and extract the plurality of image patches 208. The object detection model can use information from the rib and spine segmentation to verify that the identified location of each vertebra is anatomically feasible (e.g., within the spine and between pairs of ribs).

In some embodiments, the system 500 assesses each identified vertebra (via processing of the associated image patch 208) to identify whether the vertebra should be included in the subsequent fracture detection process or excluded. For example, a vertebra may be obstructed by a foreign (non-vertebra) object, such as electrodes or wires, additional spinal hardware, such as screws or rods, or additional anatomy, which may make fracture detection difficult for the vertebra. Accordingly, as illustrated in FIG. 3, at block 209, the system 500 may detect any foreign objects within each extracted image patch 208 to identify whether the vertebra represented win the patch 208 is obstructed. In some embodiments, the system 500 uses the detected spine, ribs, or both to determine whether a particular vertebra is obstructed by a foreign object. Based on any detected foreign objects, the system 500 may determine whether the view of the vertebra is obscured by a detected foreign object (at block 212). The system 500 may, for example, detect a foreign object based on if only part of a vertebra is visible within the extent of the image. When the view of a vertebra is obstructed by a detected foreign object, the system 500 may exclude the vertebra (the associated image patch 208) from further processing (at block 210). Alternatively, when the view of a vertebra is not obstructed by a detected foreign object, the system 500 continues to block 216. In some embodiments, the system 500 is configured to apply one or more parameters or configurations to determine whether a view of a vertebra is obstructed. For example, the system 500 may determine whether a detected foreign object obstructs a predetermined percentage of the vertebra (e.g., a predetermined percentage of the image patch 208) to determine whether there is an obstruction that warrants exclusion of the image patch 208.

In some embodiments, as part of detecting obstructions or as a separate analysis, the system 500 may also be configured to determine whether to exclude a vertebra from further processing based on the visibility of the vertebra (at block 212). Visibility can be effected by foreign objects, other anatomy, the image view represented in the image 10 (e.g., only part of a vertebra is visible within the extent of the image because the vertebra was cut off within the view), or image quality (e.g., sometimes x-rays are taken to specifically highlight other anatomy, such as the lungs or the heart, and bones, such as a vertebra, may be unfocused or blurred in the image 10). Accordingly, the system 500 can be configured to evaluate a degree of visibility of a vertebra based on one or more of the above factors to determine if the visibility is sufficient for evaluation. When the degree of visibility is not sufficient for evaluation, the system 500 may exclude the vertebra from further processing by discarding the associated image patch 208 (at block 210).

In addition to or as an alternative to identifying obstructions, visibility issues, or both, the system 500 may determine whether each vertebra was previously corrected (e.g., whether there was a previous fracture that was corrected via cement, a pin, or other intervention). For example, as illustrated in FIG. 3, at block 214, the system 500 determines, for each vertebra, whether the vertebra was previously corrected. The system 500 may use a segmentation model to identify spinal cement or augmentation (e.g., kyphoplasty, vertebroplasty, etc.) present in the spine (i.e., represented within the image 10 or a particular image patch 208), which indicates a previous fracture that was corrected. When the system 500 determines that a vertebra was previously corrected (at block 216), the system 500 excludes the vertebra from further processing (e.g., discards the associated image patch 208) (at block 210). However, when a fracture was not previously corrected, the vertebra is subject to further processing. For example, in this situation, the system 500 may proceed to block 106 (see FIG. 2). It should be understood that the system 500 may be configured to determine whether to discard a particular vertebra (an associated image patch 208) as described above in various orders. For example, in some embodiments, the system 500 may be configured to initially assess the visibility of each vertebra before detecting foreign objects or corrected fractures. The order of processing may be configured to initially assess for the most common issue and move to the least common issue. This sequence reduces the number of vertebra (image patches 208) that are analyzed. Also, in some embodiments, these checks can be performed in parallel (e.g., by the same or different systems) and only image patches 208 that are retained by each check are used during subsequent processing.

Returning to FIG. 2, after detecting the plurality of vertebrae 20 and extracting associated image patch 208 (and optionally discarding one or more image patches 208), the system 500 sequences the detected vertebrae (at block 106). Sequencing the vertebrae may include defining a particular vertebra's position with respect to other vertebra or other pieces of anatomy (e.g., ordering the vertebra from top-most vertebra to bottom-most vertebra or vice versa). Sequencing the vertebrae allows the system 500 to determine the height of each vertebra, the spacing between vertebral bodies, the location of the change or fracture within the vertebrae, the location of a vertebra within the spinal column, and the curvature of the spine and use this information as part of detecting fractures.

In particular, as illustrated in FIG. 2, at block 110, the system 500 uses the sequenced vertebrae to determine whether a fracture exists in each of the vertebra. In particular, as illustrated in FIG. 4, the system 500 can feed the ordered sequence of image patches 208 (the ordered sequence 107) into a model 108. The model 108 may include a multi-output time-distributed convolutional neural network-recurrent neural network (CNN-RNN) inference model, a convolutional neural network-long short term memory (CNN-LS™) network, or the like. These models consider not only each individual vertebra and their size and shape but also the size and shape of the vertebra relative to another vertebra within the ordered sequence 107 to distinguish natural vertebral degeneration from degeneration associated with a fracture. For example, these models can be configured to analyze and compare various attributes of a first detected vertebra (e.g., a size, a shape, a location, or a combination thereof) included in the ordered sequence of image patches 208 to various attributes of a second vertebra (e.g., a size, a shape, a location, or a combination thereof) included in the ordered sequence 107 to detect fractures. In some embodiments, the second vertebra may be adjacent to the first vertebra within the ordered sequence 107.

Based on output from the model 108, the system 500 assigns a classification to each image patch 208 (i.e., each vertebra) indicating whether the image patch 208 represents a fractured vertebra or an unfractured vertebra. One or more of these classifications can be stored for later review (e.g., by a radiologist, a physician, or the like), automatically added to a report, transmitted to one or more systems for additional processing, or the like. For example, various alerts or notifications may be generated when a vertebra is classified as being fractured to help treat a patient.

In some cases, fractures may be visible in other x-rays with views other than a frontal view. For example, factures can also be detected in lateral chest x-rays. Accordingly, some embodiments are configured to analyze multiple different image views, such as frontal and lateral views, to detect vertebral fractures. For example, the vertebral extraction and sequential analysis described above for method 100 can be separately conducted for each image type, and the output from each image type can be combined to provide a single diagnosis for each vertebra.

Figure 5:
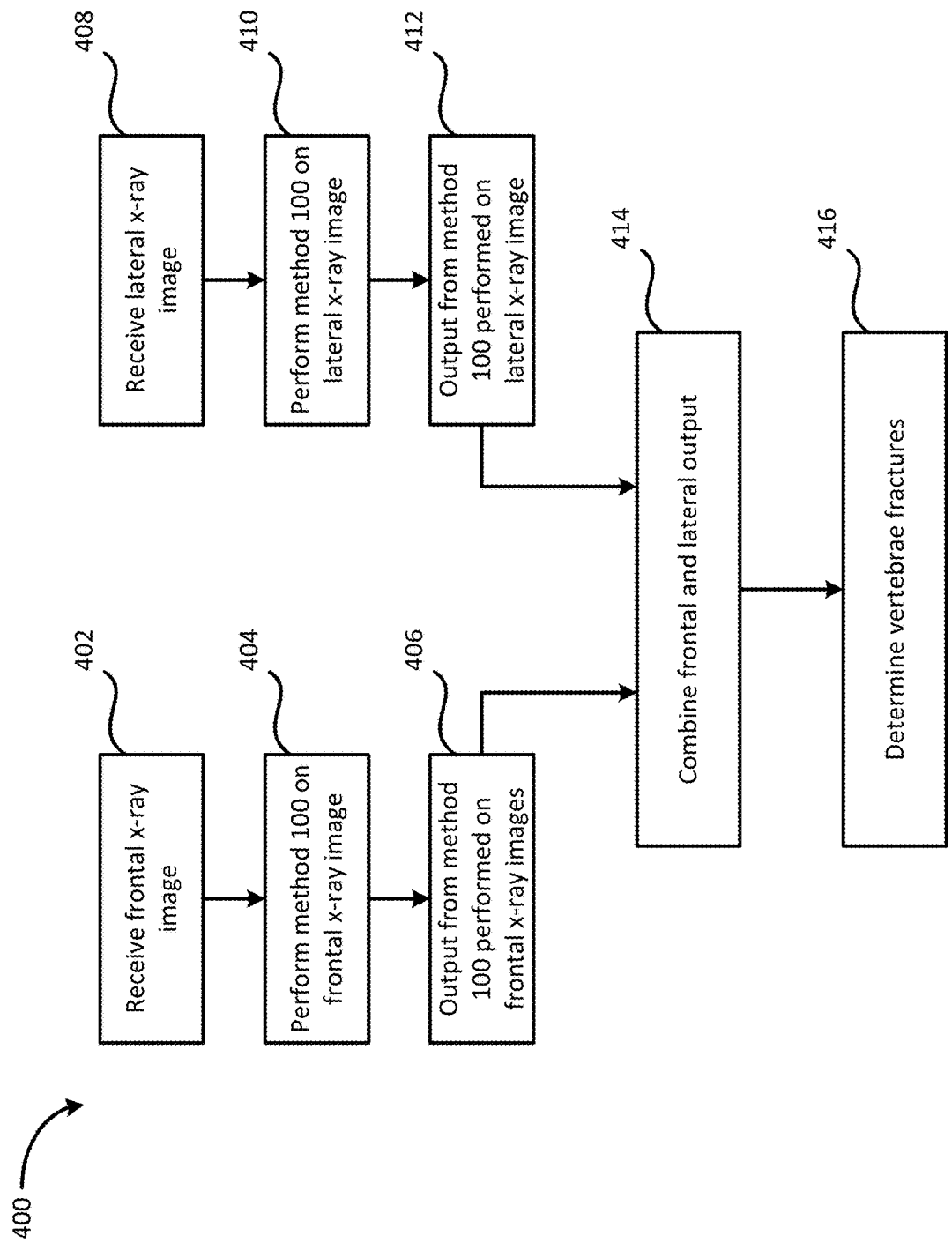
FIG. 5 illustrates a flowchart of a method of analyzing both frontal x-ray images and lateral x-ray images according to some embodiments.

For example, FIG. 5 illustrates a method 400 for using both a frontal x-ray image and a lateral x-ray image to determine vertebral fractures. The method 400 is described herein as being performed using the system 500 as described below and, in particular, via one or more electronic processors 550 that implement one or more models, such as one or more neural networks. At block 402, the system 500 receives a frontal x-ray image, such as the chest x-ray image 10. At block 404, the system 500 applies the method 100 to the frontal x-ray image as described above. Accordingly, at block 406, the system 500 receives output from applying the method 100, such as a classification (e.g., fractured or unfractured) assigned to each detected and processed vertebra within the frontal x-ray image.

At block 408, the system 500 receives a lateral x-ray image. The lateral x-ray image may be a lateral (side) view, such as a view from the left or right, of the same patient represented within the frontal chest x-ray image 10. At block 410, the system 500 applies the method 100 to the lateral x-ray image. At block 412, the system 500 receives output from applying the method 100, such as a classification (e.g., fractured or unfractured) for each detected and processed vertebra within the lateral x-ray image.

At block 414, the output of the frontal x-ray image analysis and the output of the lateral x-ray image analysis are combined. For example, in some embodiments, the system 500 uses a probabilistic inference model to combine the results. For example, the probabilistic inference model may be configured to combine the outputs by using a weighted average of probabilistic outputs from each model, where the weights are determined empirically. The probabilistic inference model may apply a weighted value to each output to determine a weighted average of the outputs. The outputs can also be combined by training one or more separate models (e.g., one or more neural networks, a mixture of experts, or the like) that learns how to combine the outputs (e.g., trained and evaluated using labeled training and testing data). This model can be configured to accept probability inputs and learn weights of the model to optimally combine these inputs and produce a correct classification output. At block 416, the presence of vertebral fractures is determined based on the combined classification, which, as noted above, can be used stored, transmitted, included in a report, used to generate an alert or notification, etc.

Although method 400 is described as using a single frontal chest x-ray image and a single lateral chest x-ray image, it should be understood that multiple frontal chest x-ray images, multiple lateral chest x-ray images, or a combination thereof may be used. For example, the results from multiple frontal chest x-ray images and the results from multiple lateral chest x-ray images may be combined in a manner as described above (at block 414). Alternatively or in addition, in some embodiments, one or more vertebra of the plurality of vertebrae may be identified in different x-ray images. For example, a first vertebra may be identified in a first frontal x-ray image, and a second vertebra may be identified in a second frontal x-ray image. For example, the system 500 may identify the x-ray image in which a specific vertebra is most visible and use the corresponding image patch 208 as described above to determine whether the vertebra includes a fracture. Similarly, the method 100 may use multiple x-ray images of a single image view by combining outputs for different images, extracting image patches from different images, or the like.

Figure 6:
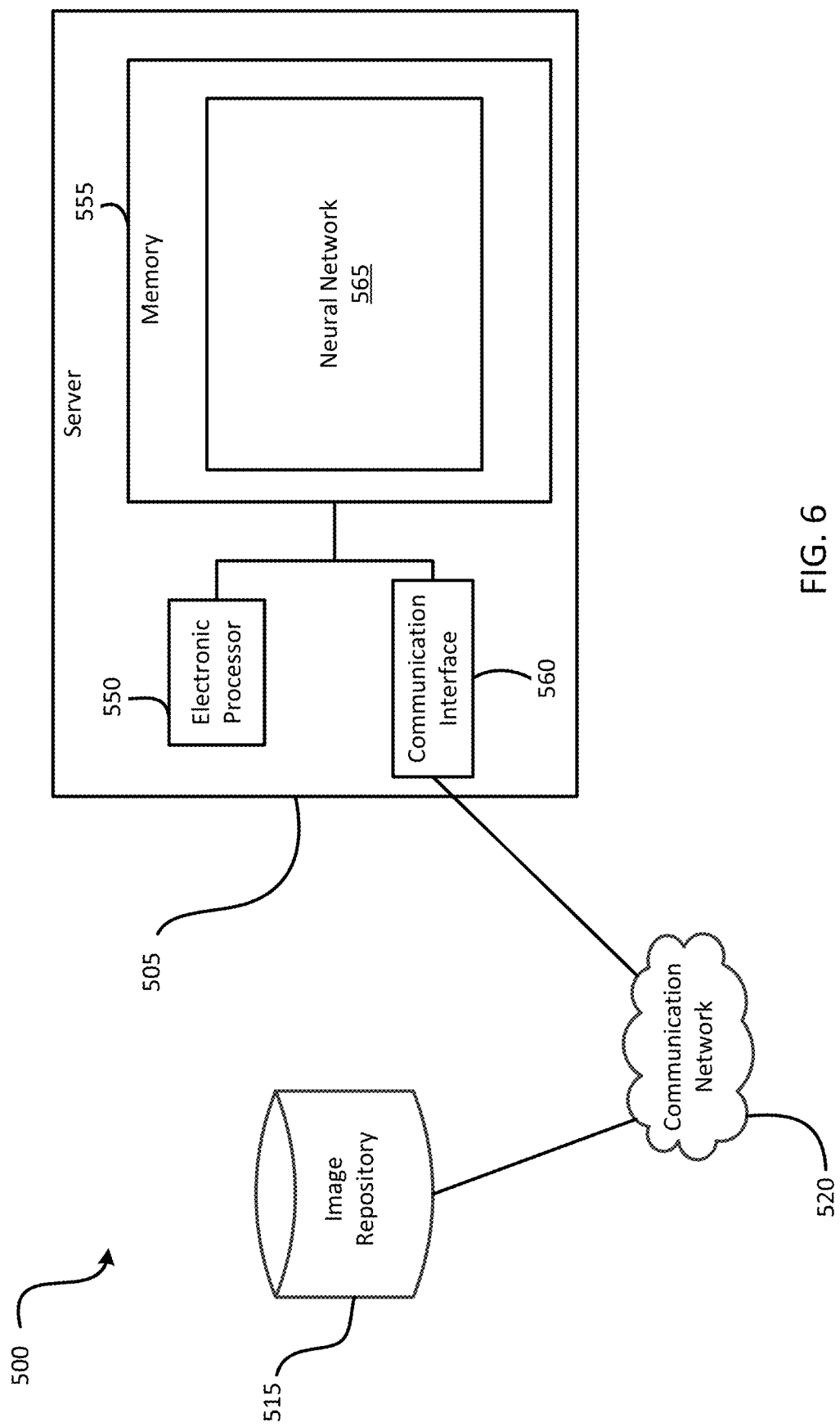
FIG. 6 illustrates a block diagram of a system for performing the methods of FIG. 2, 3, 5, or a combination thereof according to some embodiments.

It should also be understood that the functionality described herein (e.g., the methods of FIGS. 2, 3, 5, or a combination thereof) can be performed via one or more computing devices, such as one or more servers. For example, FIG. 6 illustrates a system 500 for determining a vertebra fracture according to some embodiments. As illustrated in FIG. 6, the system 500 includes a server 505 and an image repository 515. The server 505 and the image repository 515 communicate over one or more wired or wireless communication networks 520. Portions of the wireless communication networks 520 may be implemented using a wide area network, such as the Internet, a local area network, such as a Bluetooth™ network or Wi-Fi, and combinations or derivatives thereof. It should be understood that the system 500 may include more or fewer servers and the single server 505 illustrated in FIG. 6 is purely for illustrative purposes. For example, in some embodiments, the functionality described herein is performed via a plurality of servers in a distributed or cloud-computing environment. Also, in some embodiments, the server 505 may communicate with multiple image repositories or multiple reports repositories. Furthermore, in some embodiments, an image repository may be combined with a report repository and, in some embodiments, one or more of these repositories may be combined with the server 505. Also, in some embodiments, the components illustrated in system 500 may communicate through one or more intermediary devices (not shown).

In some embodiments, x-ray images are stored in the image repository 515. The image repository 515 may be, for example, a picture archiving and communication system (PACS), a cloud storage environment, or the like. The x-ray images stored in the image repository 515 are generated by an imaging modality (not shown), such as an X-ray machine. In some embodiments, the image repository 515 may also be included as part of an imaging modality.

As illustrated in FIG. 6, the server 505 includes an electronic processor 550, a memory 555, and a communication interface 560. The electronic processor 550, the memory 555, and the communication interface 560 communicate wirelessly, over wired communication channels or buses, or a combination thereof. The server 505 may include additional components than those illustrated in FIG. 6 in various configurations. For example, in some embodiments, the server 505 includes multiple electronic processors, multiple memory modules, multiple communication interfaces, or a combination thereof. Also, it should be understood that the functionality described herein as being performed by the server 505 may be performed in a distributed nature by a plurality of computers located in various geographic locations. For example, the functionality described herein as being performed by the server 505 may be performed by a plurality of computers included in a cloud computing environment.

The electronic processor 550 may be, for example, a microprocessor, an application-specific integrated circuit (ASIC), and the like. The electronic processor 550 is generally configured to execute software instructions to perform a set of functions, including the functions described herein.

The memory 555 includes a non-transitory computer-readable medium and stores data, including instructions executable by the electronic processor 550. The communication interface 560 may be, for example, a wired or wireless transceiver or port, for communicating over the communication network 520 and, optionally, one or more additional communication networks or connections.

In some embodiments, the electronic processor 550 executes a collection of different models to perform the functionality described above, some of which may include deep learning models. For example, as illustrated in FIG. 6, the memory 555 of the server 505 stores one or more models, such as a neural network 565. The neural network 565 may be, for example, a two-dimensional (2D) U-net architecture, a three-dimensional (3D) convolutional neural network (CNN), a long short-term memory (LSTM) network, or the like. The neural network 565 may be trained using a variety of frontal chest x-ray images, lateral chest x-ray images, and a combination thereof. Additionally, the neural network 565 may include a plurality of models combined to process and analyze the chest x-ray image. For example, a UNet model may segment each rib in the x-ray image 10, a second UNet model may segment the spine in the x-ray image 10, an object-detection model or segmentation model may detect and sequence the vertebrae located in the x-ray image 10, and a multi-output time-distributed convolutional neural network-recurrent neural network inference model may detect the presence and location of the vertebral fractures in the sequenced vertebrae. In some embodiments, a mask regional convolutional neural network (R-CNN) model may be used.

Various features and advantages of the embodiments are set forth in the following claims.

What is claimed is:

1. A computer-implemented method of detecting a fracture, the method comprising:
   receiving a chest x-ray image;
   identifying a plurality of vertebrae represented in the chest x-ray image;
   extracting a plurality of image patches from the chest x-ray image, each image patch of the plurality of image patches including a portion of the chest x-ray image representing one of the plurality of vertebrae identified in the chest x-ray image;
   sequencing the plurality of image patches into an ordered sequence of image patches; and
   assigning, with a deep learning model applied to the ordered sequence of image patches, a classification to each of the plurality of image patches indicating whether the image patch represents a fractured vertebra or an unfractured vertebra, wherein applying the deep learning model includes applying a time-distributed inference model to the ordered sequence of image patches.

2. The method of claim 1, further comprising:
   determining, for a vertebra represented in one of the plurality of image patches, a visibility of the vertebra; and
   in response to the visibility of the vertebra failing to satisfy a predetermined threshold, discarding the one image patch before applying the deep learning model to the ordered sequence of image patches.

3. The method of claim 1, further comprising:
   in response to detecting a correction of a previous fracture in a vertebra represented in one image patch of the plurality of image patches, discarding the one image patch before applying the deep learning model to the ordered sequence of image patches.

4. The method of claim 1, wherein applying the time-distributed inference model includes applying a time-distributed convolutional neural network and a long short term memory inference model.

5. The method of claim 1, wherein applying the deep learning model includes comparing at least one selected from a group consisting of a size, a shape, and a location of a first vertebra represented in a first image patch of the plurality of image patches included in the ordered sequence of image patches to at least one selected from a group consisting of a size, a shape, and a location of a second vertebra represented in a second image patch of the plurality of image patches included in the ordered sequence of image patches.

6. The method of claim 1, wherein receiving the chest x-ray image includes receiving one selected from a group consisting of a frontal chest x-ray image and a lateral chest x-ray image.

7. The method of claim 1, wherein receiving the chest x-ray includes receiving a frontal chest x-ray image of a patient and wherein the method further comprises:
   receiving a second chest x-ray image including a lateral chest x-ray of the patient;
   identifying a second plurality of vertebrae represented in the second chest x-ray image;
   extracting a second plurality of image patches from the second chest x-ray image, each image patch of the second plurality of image patches including a portion of the second chest x-ray image representing one of the second plurality of vertebrae identified in the second chest x-ray image;
   sequencing the second plurality of image patches into a second ordered sequence of image patches;
   assigning, with a second deep learning model applied to the second ordered sequence of image patches, a classification to each of the second plurality of image patches indicating whether the image patch represents a fractured vertebra or an unfractured vertebra; and
   combining the classification assigned to one of the plurality of image patches extracted from the chest x-ray image including the frontal chest x-ray image and the classification assigned to one of the second plurality of image patches extracted from the second chest x-ray image including the lateral chest x-ray image to generate a combined classification for a vertebra of the patient.

8. A system for detecting a fracture, the system comprising:
   an electronic processor configured to:
      receive a chest x-ray image;
      identify a plurality of vertebrae represented in the chest x-ray image;
      extract a plurality of image patches from the chest x-ray image, each image patch of the plurality of image patches including a portion of the chest x-ray image representing one of the plurality of vertebrae identified in the chest x-ray image;
      sequence the plurality of image patches into an ordered sequence of image patches; and
      assign, with a deep learning model applied to the ordered sequence of image patches, a classification to each of the plurality of image patches indicating whether the image patch represents a fractured vertebra or an unfractured vertebra, wherein applying the deep learning model includes applying a time-distributed inference model to the ordered sequence of image patches.

9. The system of claim 8, wherein the electronic processor is further configured to:
   determine, for a vertebra represented in one of the plurality of image patches, a visibility of the vertebra; and
   in response to the visibility of the vertebra failing to satisfy a predetermined threshold, discard the one image patch before applying the deep learning model to the ordered sequence of image patches.

10. The system of claim 8, wherein the electronic processor is further configured to:
    in response to detecting a correction of a previous fracture in a vertebra represented in one image patch of the plurality of image patches, discard the one image patch before applying the deep learning model to the ordered sequence of image patches.

11. The system of claim 8, wherein applying the time-distributed inference model includes applying a time-distributed convolutional neural network and a long short term memory inference model.

12. The system of claim 8, wherein applying the deep learning model includes comparing at least one selected from a group consisting of a size, a shape, and a location of a first vertebra represented in a first image patch of the plurality of image patches included in the ordered sequence of image patches to at least one selected from a group consisting of a size, a shape, and a location of a second vertebra represented in a second image patch of the plurality of image patches included in the ordered sequence of image patches.

13. The system of claim 8, wherein receiving the chest x-ray image includes receiving one selected from a group consisting of a frontal chest x-ray image and a lateral chest x-ray image.

14. The system of claim 8, wherein receiving the chest x-ray includes receiving a frontal chest x-ray image of a patient and wherein the electronic processor is further configured to:
    receive a second chest x-ray image including a lateral chest x-ray of the patient;
    identify a second plurality of vertebrae represented in the second chest x-ray image;
    extract a second plurality of image patches from the second chest x-ray image, each image patch of the second plurality of image patches including a portion of the second chest x-ray image representing one of the second plurality of vertebrae identified in the second chest x-ray image;
    sequence the second plurality of image patches into a second ordered sequence of image patches;
    assign, with a second deep learning model applied to the second ordered sequence of image patches, a classification to each of the second plurality of image patches indicating whether the image patch represents a fractured vertebra or an unfractured vertebra; and
    combine the classification assigned to one of the plurality of image patches extracted from the chest x-ray image including the frontal chest x-ray image and the classification assigned to one of the second plurality of image patches extracted from the second chest x-ray image including the lateral chest x-ray image to generate a combined classification for a vertebra of the patient.

15. Non-transitory computer-readable medium storing instructions that, when executed by an electronic processor, perform a set of functions, the set of functions comprising:
    receiving a chest x-ray image;
    identifying a plurality of vertebrae represented in the chest x-ray image;
    extracting a plurality of image patches from the chest x-ray image, each image patch of the plurality of image patches including a portion of the chest x-ray image representing one of the plurality of vertebrae identified in the chest x-ray image;
    sequencing the plurality of image patches into an ordered sequence of image patches; and
    assigning, with a deep learning model applied to the ordered sequence of image patches, a classification to each of the plurality of image patches indicating whether the image patch represents a fractured vertebra or an unfractured vertebra, wherein applying the deep learning model includes applying a time-distributed inference model to the ordered sequence of image patches.

16. The non-transitory computer-readable medium of claim 15, wherein the set of functions further comprises:
    determining, for a vertebra represented in one of the plurality of image patches, a visibility of the vertebra; and
    in response to the visibility of the vertebra failing to satisfy a predetermined threshold, discarding the one image patch before applying the deep learning model to the ordered sequence of image patches.

17. The non-transitory computer-readable medium of claim 15, wherein the set of functions further comprises:
    in response to detecting a correction of a previous fracture in a vertebra represented in one image patch of the plurality of image patches, discarding the one image patch before applying the deep learning model to the ordered sequence of image patches.

18. The non-transitory computer-readable medium of claim 15, wherein applying the deep learning model includes comparing at least one selected from a group consisting of a size, a shape, and a location of a first vertebra represented in a first image patch of the plurality of image patches included in the ordered sequence of image patches to at least one selected from a group consisting of a size, a shape, and a location of a second vertebra represented in a second image patch of the plurality of image patches included in the ordered sequence of image patches.

19. The non-transitory computer-readable medium of claim 15, wherein receiving the chest x-ray image includes receiving one selected from a group consisting of a frontal chest x-ray image and a lateral chest x-ray image.

20. The non-transitory computer-readable medium of claim 15, wherein receiving the chest x-ray includes receiving a frontal chest x-ray image of a patient and wherein the set of functions further comprises:
    receiving a second chest x-ray image including a lateral chest x-ray of the patient;
    identifying a second plurality of vertebrae represented in the second chest x-ray image;
    extracting a second plurality of image patches from the second chest x-ray image, each image patch of the second plurality of image patches including a portion of the second chest x-ray image representing one of the second plurality of vertebrae identified in the second chest x-ray image;
    sequencing the second plurality of image patches into a second ordered sequence of image patches;
    assigning, with a second deep learning model applied to the second ordered sequence of image patches, a classification to each of the second plurality of image patches indicating whether the image patch represents a fractured vertebra or an unfractured vertebra; and combining the classification assigned to one of the plurality of image patches extracted from the chest x-ray image including the frontal chest x-ray image and the classification assigned to one of the second plurality of image patches extracted from the second chest x-ray image including the lateral chest x-ray image to generate a combined classification for a vertebra of the patient.

* * * * *